Figure 1:
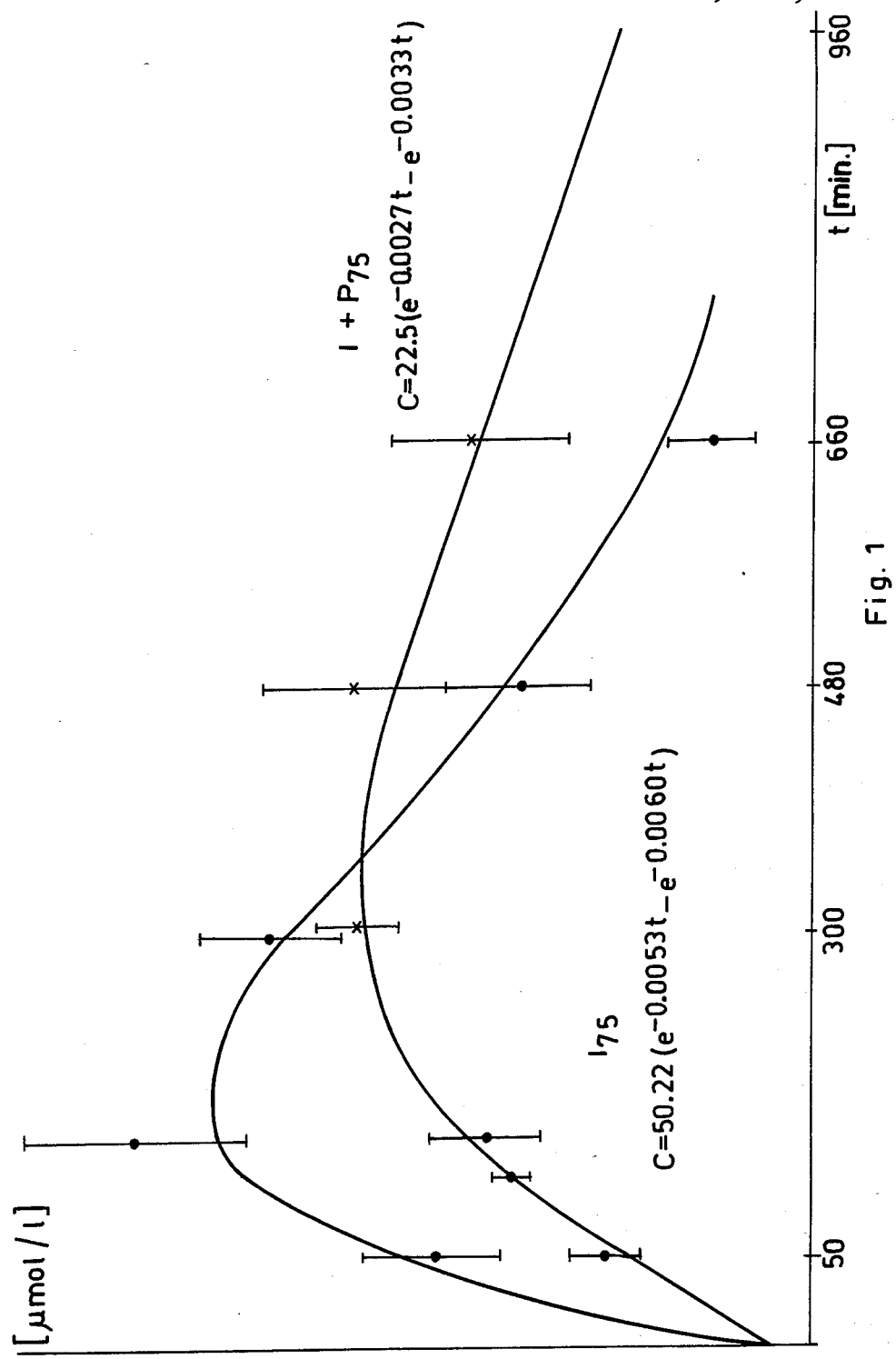

United States Patent [19]

Pongor née Csákvári et al.

[11] Patent Number: 4,556,563

[45] Date of Patent: Dec. 3, 1985

[54] SYNERGISTIC ANTIPHLOGISTIC COMPOSITIONS AND METHODS OF USE

[75] Inventors: Marianna Pongor née Csákvári; Gábor Nagy; Gábor Horváth; Mária Dávid née Kenéz; Sándor Bozsóky; Sándor Virág, all of Budapest; Katalin Mármarosi née Kellner, Biatorbágy, all of Hungary

[73] Assignee: Chinoin Gyogyszer es Vegyeszeti Termekek Gyara Rt., Budapest, Hungary

[21] Appl. No.: 474,750

[22] Filed: Mar. 10, 1983

[30] Foreign Application Priority Data

Mar. 31, 1982 [HU] Hungary ................................. 976/82

[51] Int. Cl.[4] ..................... A61K 31/60; A61K 31/505
[52] U.S. Cl. ..................... 514/258; 514/966; 514/960
[58] Field of Search ................................. 424/274, 251

[56] References Cited

PUBLICATIONS

Hippius et al., Zbl. Pharm. 119 (1980), Part 2, pp. 147–157, which is equivalent to Chem. Abstracts (R) of Record.
Farago et al., Zbl. Pharm. 122 (1983), Part 1, 19–21.
Chem. Abst. 92-180h, (1980).
Chem. Abst. 94-52988p, (1981).

*Primary Examiner*—Stanley J. Friedman
*Attorney, Agent, or Firm*—Karl F. Ross; Herbert Dubno

[57] ABSTRACT

The invention relates to synergistic antiphlogistic pharmaceutical compositions comprising a pyrido [1,2-a]-pyrimidine derivative of the Formula I

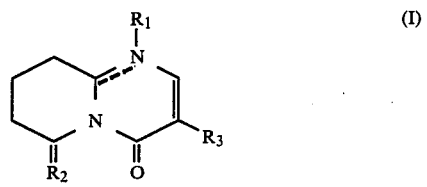

wherein $R^1$ and $R^2$ are lower alkyl and $R^3$ stands for lower alkoxycarbonyl or carbamoyl and the dotted line represents an optionally hydrogenated band or a salt or quaternary salt thereof and 1-[p-chloro-benzoyl]-2-methyl-5-methoxy-indolyl-3-acetic acid of the Formula II

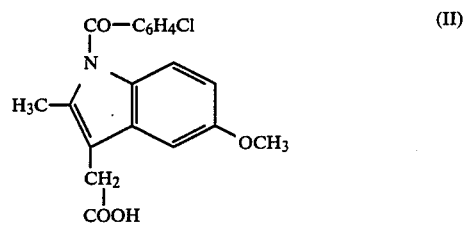

The advantage of the compositions is that as a result of the synergistic activity of the compound of the Formula I, the antiphlogistic Indomethacin of the Formula II can be administered in a significantly lower doses and consequently the unfavorable side effects of the latter compound are mitigated.

8 Claims, 2 Drawing Figures

SYNERGISTIC ANTIPHLOGISTIC COMPOSITIONS AND METHODS OF USE

FIELD OF THE INVENTION

This invention relates to synergistic anti-phlogistic compositions and a process for the preparation thereof.

BACKGROUND OF THE INVENTION

In the treatment of chronic rheumatic diseases in practice non-steroidal anti-phlogistic agents are used almost exclusively. The drug 1-(p-chloro-benzoyl)-2-methyl-5-methoxy-indolyl-3-acetic acid (Indomethacin) is the most frequently used agent, generally in a daily dosage of 75 mg. Although Indomethacin is the most widespread antiphlogistic agent now in use, its application is strongly limited by the undesired side-effects thereof which occur even after a relatively short treatment period. The following harmful side effects can be mentioned: in effective doses Indomethacin damages the mucosa of the stomach, it causes gastric ulcers and exhibits further detrimental side effects on the haematopoietic system.

OBJECT OF THE INVENTION

The object of the present invention is to provide pharmaceutical compositions which effect the absorption and excretion properties of Indomethacin in an advantageous manner and thus enable the decrease of the pharmaceutically effective dose thereof to such a low level that the harmful side effects of Indomethacin do not manifest themselves.

DESCRIPTION OF THE INVENTION

According to the present invention there are provided synergistic antiphlogistic pharmaceutical compositions comprising a pyrido[1,2-a]pyrimidine derivative of the Formula I

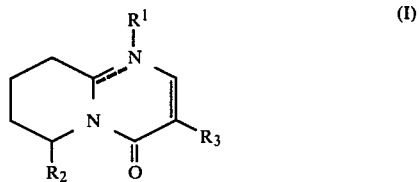

(wherein $R^1$ and $R^2$ are lower alkyl and $R^3$ stands for lower alkoxycarbonyl or carbamoyl and the dotted line represents an optionally hydrogenated bond) or a salt or quaternary salt thereof and 1-(p-chloro-benzoyl)-2-methyl-5-methoxy-indolyl-3-acetic acid of the Formula II

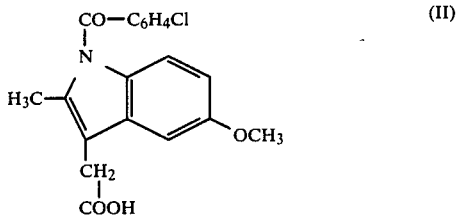

or a salt thereof in admixture with suitable inert nontoxical solid or liquid pharmaceutical carriers.

The present invention is based on the discovery that synergism exists between the compounds of the Formula I or salts or quaternary salts thereof on the one hand (British patent specification No. 1 209 946 and Hungarian patent specification No. 158 085) and Indomethacin on the other. In other terms the compounds of the Formula I or salts or quaternary salts thereof exert a synergistic effect on the anti-phlogistic activity of Indomethacin. Under the effect of a compound of the Formula I the curative dose of Indomethacin can be reduced to half of the original value and in such dosages the undesired side effects become about four to six times weaker. It is known that the compounds of the Formula I possess analgesic properties.

The term "lower alkyl" used throughout the specification relates to straight or branched chained saturated hydrocarbon groups having 1-4 carbon atoms (e.g. methyl, ethyl, n-propyl, isobutyl, etc.).

The salts and quaternary salts of the compounds of the Formula I can contain any pharmaceutically acceptable anion (e.g. inorganic anions, such as nitrate, chloride, bromide or sulfate ion or organic anions such as methosulfate or ethyl sulfate ion etc.).

According to a preferred embodiment of the present invention the synergistic compositions of the present invention contain 1,6-dimethyl-3-carbethoxy-4-oxo-6,7,8,9-tetrahydro-pyrimidazolium-methosulfate (referred to hereinafter as Probon) as compound of the Formula I.

The biological pharmacokinetic properties are determined on the basis of human clinical tests. Synergistic activity is established by measuring the blood level with the aid of UV spectrophotographical methods.

In the tests men and women aged between 27 and 63 years and suffering from mild and medium grave locomotor diseases were used. Hepatic and renal diseases and serious circulatory disorders were regarded as disqualification. The test persons received a normal hospital diet.

The test substances were administered orally in the following doses:

Group I: 75 mg. of Indomethacin, in one portion.

Group II: The patients belonging to group I did not receive any drugs for 3 days, thereafter 75 mg. of Indomethacin and 300 mg. of Probon were simultaneously administered and the blood-level was subsequently determined.

Group III: The patients received four times 25 mg. of Indomethacin for 3 days and blood sampling was started simultaneously with the administration of the first dose of the fourth day (0 minute sample).

Group IV: The patients belonging to group III did not receive any drugs for 3 days, thereafter the administration of the drugs was started in the same manner as disclosed above except that during each administration 300 mg. of Probon were introduced too.

The results of the above tests are summarized in the following Tables 1 and 2.

TABLE 1

| | Blood level μmole/l Administration | | | | | | | | | | | |
|---|---|---|---|---|---|---|---|---|---|---|---|---|
| | 75 mg. of Indomethacin | | | | | | 75 mg. of Indomethacin + 300 mg. of Probon | | | | | |
| | Time of blood sampling | | | | | | | | | | | |
| No. | 60' | 150' | 300' | 480' | 660' | 780' | 60' | 120' | 150' | 300' | 480' | 660' | 960' |
| 1. | 0.96 | 5.73 | | 0.89 | 0.87 | 0.00 | 0.59 | 1.03 | 1.79 | 1.29 | 1.03 | 1.11 | 0.00 |
| 2. | 1.35 | 2.88 | 3.52 | 2.24 | 0.00 | 0.00 | 0.84 | 1.15 | 0.20 | 1.79 | 2.57 | 0.80 | 0.00 |
| 3. | 1.88 | 2.91 | 1.90 | 0.17 | 0.17 | 0.00 | | | 1.57 | 2.01 | 3.13 | 1.83 | 0.00 |
| 4. | | 2.88 | 2.74 | 2.57 | 0.36 | | | | 1.12 | 2.15 | 2.91 | | |
| 5. | | 1.45 | 1.20 | 0.48 | 0.42 | | | | 1.79 | 2.24 | 1.68 | | |
| 6. | | 1.57 | 1.87 | 0.14 | | | | | 0.78 | 1.29 | 1.68 | | |
| 7. | | 3.35 | 1.90 | 1.57 | | | | | 0.00 | 0.67 | 0.00 | | |
| 8. | | 2.24 | 2.68 | 0.84 | | | | | 1.68 | 2.24 | 1.68 | | |
| 9. | | 0.98 | 0.98 | 0.48 | | | | | 1.82 | 1.90 | 0.00 | | |
| 10. | | 1.79 | 1.45 | 1.45 | | | | | 1.20 | 1.45 | 2.38 | | |
| Average | 1.40 | 2.58 | 2.03 | 1.08 | 0.36 | 0.00 | 0.72 | 1.09 | 1.20 | 1.70 | 1.70 | 1.25 | 0.00 |
| Average standard deviation | 0.27 | 0.43 | 0.27 | 0.27 | 0.15 | | 0.13 | 0.06 | 0.21 | 0.16 | 0.35 | 0.31 | |

TABLE 2

| | Administration | | | | | | | | | | | |
|---|---|---|---|---|---|---|---|---|---|---|---|---|
| | 4 × 25 mg of Indomethacin for 3 days | | | | | | 4 × mg. of Indomethacin 300 mg of Probon for 3 days | | | | | |
| | Time of blood sampling | | | | | | | | | | | |
| No. | 0 | 150' | 300' | 480' | 660' | 840' | 0 | 150' | 300' | 480' | 960' | 1440' |
| 1. | 0.76 | 1.03 | 1.25 | 0.98 | 0.81 | 0.00 | 2.68 | 2.12 | 1.12 | 2.01 | | |
| 2. | 0.92 | 1.72 | 1.34 | 1.03 | 0.50 | 0.00 | 1.03 | 0.89 | 1.03 | 1.48 | | |
| 3. | 1.83 | 2.15 | 1.37 | 0.49 | 0.29 | 0.00 | 1.37 | 0.98 | 2.52 | 1.34 | | |
| 4. | 3.07 | 3.55 | 2.68 | 1.57 | | | 1.57 | 1.57 | 0.73 | 0.73 | | |
| 5. | 0.89 | 2.32 | 2.24 | 1.68 | | | 1.42 | 2.65 | 1.42 | 2.60 | 0.60 | 0.00 |
| 6. | 2.12 | 1.45 | 2.01 | 0.70 | | | 1.52 | 2.44 | 2.44 | 0.70 | 0.39 | 0.29 |
| 7. | 0.70 | 2.88 | 1.79 | 2.32 | | | 1.72 | 2.44 | 2.65 | 1.01 | 0.29 | 0.00 |
| 8. | 2.46 | 2.46 | 1.57 | 1.68 | | | 0.70 | 1.72 | 1.49 | 2.70 | 0.18 | 0.00 |
| Average | 1.59 | 2.20 | 1.78 | 1.31 | 0.53 | 0.00 | 1.50 | 1.85 | 1.68 | 1.57 | 0.37 | 0.07 |
| Standard deviation of average | 0.33 | 0.28 | 0.18 | 0.22 | 0.15 | | 0.20 | 0.24 | 0.27 | 0.28 | 0.08 | 0.07 |

The results were evaluated by the "two compartment" mathematical model frequently used in pharmacokinetical tests (Kinetics of Drug Action, Ed. 3. van Rossum Springer, Verlag Berlin, Heidelberg, New York 1977). The experimental data were approximated with the aid of the following function:

$$y = p_3(e^{-p_2 t} - e^{-p_1 t})$$

The optimal parameter values were selected by minimalizing the sum of the squares of the deviations.

Some data were neglected from the calculations. If the individual blood level curve gave rise to suspicion of a measurement error and at the same time the Dixon test [W. I. Dixon: Processing data for outliers, Biometrics 9, (1953) 74–89 Appendix 89] proved that the data was beyond the characteristic distribution of the group ordered to the identical blood sampling time, the said value was not taken into consideration.

In the case of continuous administration the point of time at which the curve starts must be determined (theoretical value belonging to 0 blood level). The value estimated by using the approximately parameters occurred in both cases in the environment of 90 minutes so that in the calculations a transformation of "$t = t' + 90$ minutes" was used.

The determination of the parameters suitable for the comparison of the biological utilization was carried out graphically (characteristic features of peak maxima, area below the curve) and the half-period was calculated from the relation $$T = \frac{\ln 2}{p_1}$$

In FIG. 1 the average blood levels and standard deviation thereof measured by the administration of 75 mg. of Indomethacin (abbreviation: $I_{75}$) and 75 mg. of Indomethacin + 300 mg. of Probon (abbreviation: $I + P_{75}$) and the approximating function are shown.

Figure 2:
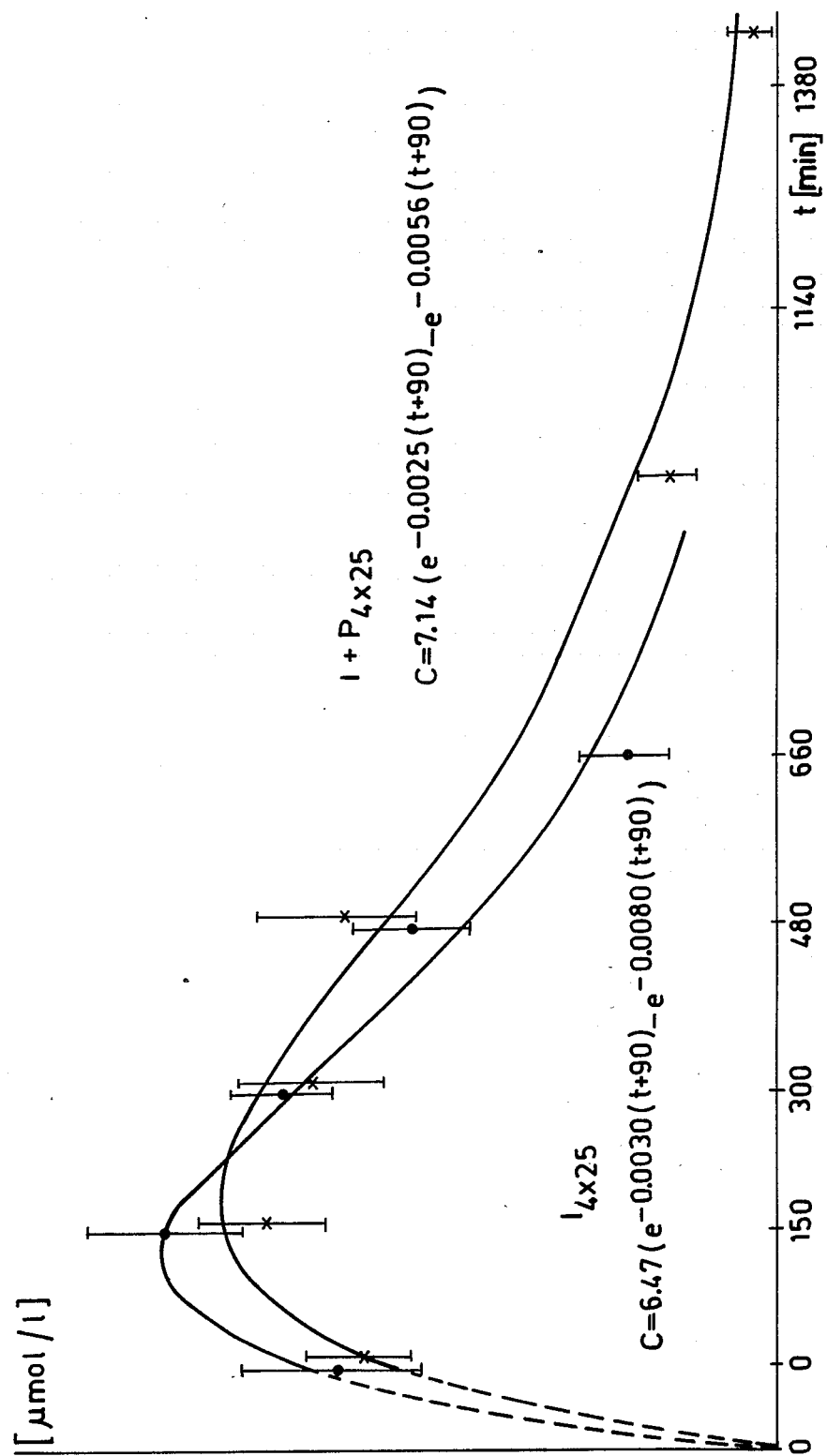

In FIG. 2 the same data are displayed, measured in the case of continuous administration of Indomethacin (abbreviation: $I_{4 \times 25}$) and that of Indomethacin + Probon ($I + P_{4 \times 25}$).

The characteristic data read off the curves are disclosed in Table 3 (the dimensions of the values can be taken from the Figures).

TABLE 3

| Administration | Maximal blood level | Point of time of maximum | Half period | Area below the curve | Blood level in the 8th hour | "t" test |
|---|---|---|---|---|---|---|
| $I_{75}$ | 2.29 | 180 | 115.5 | 131 | 1.14 | $p < 5\%$ |
| $I + P_{75}$ | 1.66 | 330 | 210.0 | 148 | 1.54 | |
| $I_{4 \times 25}$ | 2.24 | 110 | 86.6 | 96 | 1.10 | |
| $I + P_{4 \times 25}$ | 2.02 | 180 | 126.0 | 117 | 1.41 | $p < 5\%$ |

From Table 3 the following conclusions can be drawn:
1. Under the effect of Probon the maximal blood level of Indomethacin decreases and this—together with the enlargement of the area below the curve—points to a more uniform active ingredient distribution.
2. The fact, that under the effect of Probon the point of time belonging to the maximal concentration occurs later, also shows a more uniform blood level change of Probon.
3. Both the increased half-period (under the effect of Probon) and the enlargement of the area below the curve indicate that more uniform distribution of Indomethacin in blood is advantageous because the blood level falls within the effective interval for a longer period of time.
4. In order to examine the possibility of administering the drug three times a day, blood levels measured 8 hours after the administration of the drug were compared and it was found that Indomethacin blood level was significantly higher when the active ingredients were administered together.

Synergism between Indomethacin and Probon was tested by means of human clinical test. In the said test 50 patients were used, according to the following distribution of diagnosis: spondylarthritis ankylopoetica: 21, coxarthrosis: 11, polyarthritis chronica progressiva: 3, spondylosis universalis: 12, status post laminectomia: 2, cervicalis syndroma: 1.

The active ingredients were administered according to the so-called double control test principle. The patients received the following treatment:
I. week: 100 mg. of Indomethacin,
II. week: 50 mg. of Indomethacin + 900 mg. of Probon
III. week: 50 mg. of Indomethacin + 150 mg. of Novamidazophen [(2,3-dihydro-1,5-dimethyl-3-oxo-2-phenyl-1-(4-pyrazol-4-yl)-methylamino)methane sulfonic acid].

80% of the patients judged the combination of Indomethacin + Probon as preferable. In 3 instances the Indomethacin dose was decreased to 25 mg. per day and in one instance it was omitted. In none of the cases was it necessary to increase the Indomethacin dose.

In four cases we stopped Probon administration for some days. All the patients reported deficiency symptoms. As control a combination of Indomethacin + Novamidazophen was used: in 6 cases gastrointestinal disorders and in 2 cases skin symptoms were observed and in 3 cases the patients asked for the administration of the previous combination due to increased pain sensation.

Synergistic effect was also tested by means of a further three weeks' drug administration by using a further double control human test.

The following groups were used:
I = 41 patients received a daily 75 mg. dose of Indomethacin
II = 39 patients were administered a daily 25 mg. of Indomethacin and 3 × 500 mg. of Novamidazophen.
III = 46 patients were administered a daily 15 mg. of Indomethacin and 200 mg. of Probon.

The tests were carried out on patients suffering from chronic rheumatoid arthritis, morbus Bechterew, spondylosis, spondylarthrosis, arthrosis, periarthritis humeroscapularis, myalgia.

At the beginning and at the end of the treatment the erythrocite sedimentation, complete blood count, hepatic function, urine and latex test (in the case of rheumatic arthritis) were determined, objective laboratory tests were carried out and the patients underwent subjective evaluation. According to the objective laboratory tests in the said three groups the percentage of the recovered and significantly improved patients was as follows:
I. 26.5%
II. 38.5%
III. 43.5%.

The subjective relief of pain observed in the first 30 minutes after drug administration gave the following results in the groups (the results were expressed as a percentage of the patients who reported relief of pain):
I. 37%
II. 33%
III. 48%.

Relief of pain ceased after 4 hours. In the groups the following results were obtained (as a percentage of the treated patients):
I. 75%
II. 74.5%
III. 80.5%

Thus it can be stated that in group III relief of pain occurs earlier but lasts longer than in the other two groups.

The observations relating to the side effects are summarized in the following Table. The results are expressed as percentage of all the treated patients:

| Group | Total side effects | From these, strong side effects |
| --- | --- | --- |
| I. | 34% | 50% |
| II. | 29% | 27.2% |
| III. | 30.5% | 7.8% |

It can be stated from the above data that a further advantage of the synergistic composition according to the present invention is that the unfavorable side effects of Indomethacin are not synergized, but to the contrary, mitigated.

The sparing effect of Probon and Indomethacin is proved by clinical tests too. Thus the dosage of Indomethacin can be reduced to one half of the original value by administering the same in combination with Probon. By this method the unfavorable side effects can be reduced to from one fourth to one sixth of the original values and this constitutes a highly important and significant advance in rheumatological therapy.

In the compositions of the present invention the ratio of the active components can vary within a wide range. Thus it is preferred to use 10–50 parts, particularly 12–30 parts by weight of a compound of the Formula I or a salt or quaternary salt thereof, related to 1 part by weight of compound of the Formula II.

The compositions of the present invention can be preferably finished in the form of tablets, coated tablets, sustained-release tablets, suppositories or capsules.

According to a further feature of the present invention there is provided a process for the preparation of pharmaceutical compositions which comprises admixing a compound of the Formula I or a salt or quaternary salt thereof with the compound of the Formula II or a salt thereof and inert non-toxical solid or liquid pharmaceutical carriers and converting the same into pharmaceutical compositions by methods known per se.

It is preferred to use both the compound of the Formula I and the compound of the Formula II in a crystalline finely powdered form.

The said process is carried out by methods of pharmaceutical industry known per se.

One may proceed preferably by uniformly wetting a mixture of the compound of the Formula I and the compound of the Formula II of a suitable weight ratio with a suitable amount—preferably one-tenth volume—of a suitable solvent—preferably chloroform or isobutanol—in a suitable apparatus by kneading and mixing, drying the moist mixture and finishing the same in a known manner.

According to a further embodiment of the process of the present invention the mixture of the active ingredients is obtained by dissolving both active ingredients used in a suitable ratio, or dissolving one of the components in crystalline form in the solution of the other component.

SPECIFIC EXAMPLES

Further details of the present invention are to be found in the Examples without limiting the same to the said Examples.

EXAMPLE 1

Tablets 25 kg. of Probon and 1.5 kg. of Indomethacin (crystalline particle size about 0.1 mm.) are admixed in a plant mixer with 6.9 g. of crystalline cellulose, 0.1 kg. of hydrophobic and 0.2 kg. of hydrophilic colloidal silicic acid powder, whereupon the mixture is wetted and homogenized with a solution of 0.3 kg. of polyvinyl pyrrolidone and 3 kg. of isopropanol. The moist mass is formulated on a granulating machine and dried. After re-granulation it is homogenized with a mixture of 0.3 kg. of stearic acid and 0.7 kg. of talc and pressed into tablets weighing 350 mg. by using medium pressure under dry atmosphere.

EXAMPLE 2

Coated tablets

In a plant apparatus a suspension liquid of the following composition is applied onto tablets prepared according to Example 1 (100,000 tablets, 35 kg.) by known methods: A solution containing 2 kg. of coating resin, 500 g. of titanium dioxide, 100 g. of hydrophilic colloidal silicic acid, completed to 10 l. with propanol.

EXAMPLE 3

Suppositories

A powdered mixture of 3 kg. of Probon and 0.3 kg. of Indomethacin (particle size 0.1–0.06 mm.) is homogenized with 0.25 kg. of hydrophilic colloidal silicic acid whereupon it is homogenized with 21450 g. of a synthetic melt suppository mass. From the warm and homogenous mass suppositories weighing 2.5 g. are obtained.

EXAMPLE 4

Capsules

The granules prepared according to Example 1 are regranulated and homogenized with a mixture of 0.6 kg. of strearic acid and 0.4 kg. of talc. From the mixture thus obtained capsules weighing 350 mg. are prepared on an encapsulating machine. The capsules are packed under the exclusion of moisture.

We claim:

1. A synergistic, antiphlogistic pharmaceutical composition comprising a compound of the Formula (I)

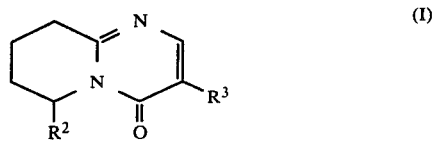

wherein
$R^2$ is lower alkyl, and
$R^3$ is lower alkoxycarbonyl, or a pharmaceutically acceptable acid addition or quaternary ammonium salt thereof, and indomethacin of the Formula (II)

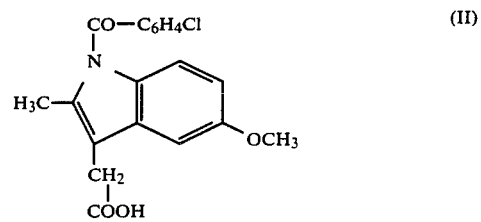

or a pharmaceutically acceptable salt thereof, in admixture with a pharmaceutically acceptable inert carrier wherein the weight ratio is 10 to 50 parts of the compound of the Formula (I) to 1 part of the indomethacin of the Formula (II).

2. A synergistic, antiphlogistic pharmaceutical composition comprising a compound of the formula (I)

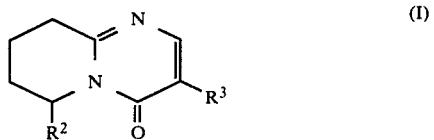

wherein
$R^2$ is lower alkyl, and
$R^3$ is lower alkoxycarbonyl, or a pharmaceutically acceptable acid addition or quaternary ammonium salt thereof, and indomethacin of the Formula (II)

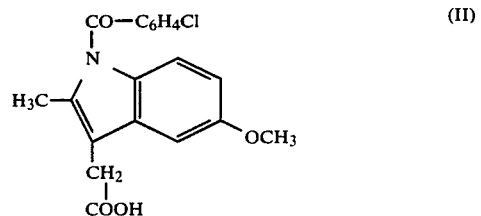

or a pharmaceutically acceptable salt thereof, in admixture with a pharmaceutically acceptable inert carrier wherein the weight ratio is 3 to 4 parts of the compound of the Formula (I) to 1 part of the indomethacin of the Formula (II).

3. The pharmaceutical composition defined in claim 1 wherein the pharmaceutically acceptable quaternary ammonium salt of the compound of the Formula (I) is 1,6-dimethyl-3-carbethoxy-4-oxo-6,7,8,9-tetrahydro-homopyrimidazolium-methosulfate.

4. The pharmaceutical composition defined in claim 2 wherein the pharmaceutically acceptable quaternary ammonium salt of the compound of the Formula (I) is 1,6-dimethyl-3-carbethoxy-4-oxo-6,7,8,9-tetrahydro-homopyrimidazolium-methosulfate.

5. The pharmaceutical composition defined in claim 1 for oral or rectal administration, in the form of tablets, coated tablets, sustained-release tablets, capsules or suppositories.

6. The pharmaceutical composition defined in claim 2 for oral or rectal administration, in the form of tablets, coated tablets, sustained-released tablets, capsules or suppositories.

7. A method of treating an inflammatory condition in a susceptible subject comprising administering to the subject in dosage form a pharmaceutically effective amount of the pharmaceutical composition defined in claim 1.

8. A method of treating an inflammatory condition in a susceptible subject comprising administering to the subject in dosage form a pharmaceutically effective amount of the pharmaceutical composition defined in claim 2.

* * * * *